United States Patent
Fardeau

(10) Patent No.: US 7,212,280 B1
(45) Date of Patent: May 1, 2007

(54) DEVICE FOR MEASURING THE DIMENSION AND CONTROLLING OF DEFECTS IN OPTICAL FIBRES DURING PRODUCTION

(76) Inventor: Jean-François Fardeau, Chemin de Bellepeire, 13170 Les Pennes Mirabeau (FR)

( * ) Notice: Subject to any disclaimer, the term of this patent is extended or adjusted under 35 U.S.C. 154(b) by 0 days.

(21) Appl. No.: 09/914,729

(22) PCT Filed: Apr. 7, 2000

(86) PCT No.: PCT/FR00/00889

§ 371 (c)(1),
(2), (4) Date: Jun. 11, 2002

(87) PCT Pub. No.: WO00/62013

PCT Pub. Date: Oct. 19, 2000

(30) Foreign Application Priority Data

Apr. 8, 1999 (FR) .................................. 99 04553

(51) Int. Cl.
*G01N 21/00* (2006.01)
(52) U.S. Cl. .................................................. 356/73.1
(58) Field of Classification Search ...................... None
See application file for complete search history.

(56) References Cited

U.S. PATENT DOCUMENTS

| | | | |
|---|---|---|---|
| 4,653,322 A | 3/1987 | Locante | |
| 4,847,509 A * | 7/1989 | Millet et al. | 250/559.24 |
| 5,283,628 A * | 2/1994 | Dotson et al. | 356/496 |
| 5,513,004 A | 4/1996 | Naqwi et al. | |

FOREIGN PATENT DOCUMENTS

EP           0 608 538           8/1994

\* cited by examiner

*Primary Examiner*—Tu T. Nguyen
(74) *Attorney, Agent, or Firm*—Cantor Colburn LLP

(57) ABSTRACT

Disclosed is a device for absolute, high-speed measurement of a diameter of an optical fiber and for detecting defects in the fiber, comprising two complementary signal processing systems including first and second sensors and first and second processing boards wherein angular calibration of the sensors is performed by directly deducing the absolute diameter of the fiber from the equations (4) and (7):

$$f(n,\theta)=\sin(\theta/2)+[n^2+1-2*n*\cos(\theta/2)]^{1/2} \quad (4)$$

$$M=[A/(B+\theta)]*[1+\sin^2\{N(D,\theta)*\pi+\phi\}], \quad (7)$$

in which n represents N1 index of a substance, θ is a measurement angle, D is outer diameter, A is a signal amplitude in volts, B is a measurement angle, and M is a signal amplitude.

8 Claims, 6 Drawing Sheets

Normal signal for a 125 μm glass fiber               Figure 3
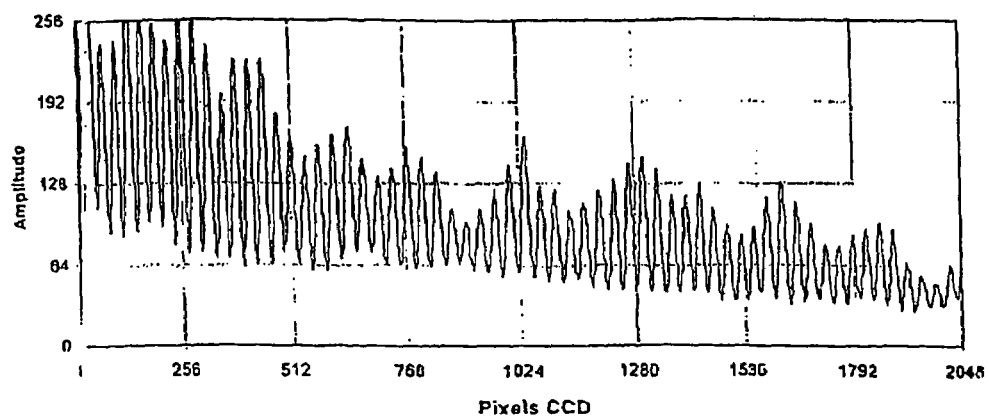
Figure 4    Signal from an uncoated 125 μm fiber with 4.8 μm "air-line" in the center
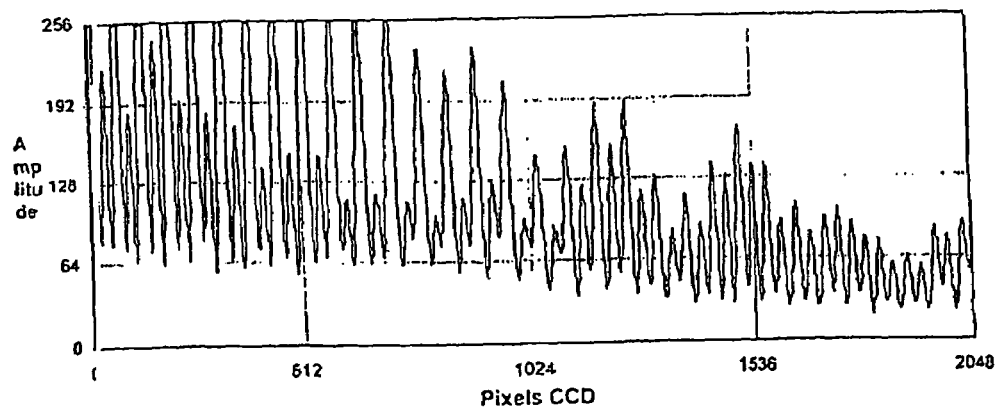

Disturbance signal

Keys: 1) Analog processing; 2) Counter; 3) D/A converter; 4) Adder; 5) D/A converter; 6) Rapid digital output 12 bits; 7) Double multiplexer; 8) Arctangent (s1/s2); 9) Rapid analog output Key- 1: if Keys: 1) Fiber; 2) Laser bundle; 3) Rapid analog outputs; 4) Absolute diameter; 5) Defect detection; 6) RS332 series input and output link Keys: 1) Period evolution; 2) Angle (degree)

Keys: 1) Mirror clamping position; 2) Optical fiber axis; 3) Laser axis reference position

DEVICE FOR MEASURING THE DIMENSION AND CONTROLLING OF DEFECTS IN OPTICAL FIBRES DURING PRODUCTION

BACKGROUND OF THE INVENTION

1. Field of the Invention

Disclosed is a method and design for an apparatus intended for absolute, high-speed measurement of the diameter of transparent fibers and for controlling internal and superficial defects.

2. Description of Related Art

Since 1970, much effort has been devoted to studying the propagation of light perpendicularly to the axis of the fiber. Over the years, this work has yielded many methods and solutions for dimensional measuring of fibers and controlling defects. Among these studies, we referred to:

[1] Saint-Etienne University Thesis, by Lionel Delauney, Mar. 28, 1986
[2] U.S. Pat. No. 3,982,816 by Laurence S. Watkins, Sep. 28, 1976.
[3] U.S. Pat. No. 4,027,977 by Ralph E. Frazee, Jun. 7, 1977
[4] U.S. Pat. No. 4,280,827 by Edward F. Murphy, Jul. 28, 1981.
[5] U.S. Pat. No. 4,176,961 by Ralph E. Frazee, Dec. 4, 1979.
[6] EP 0 549 914 B1, by Leslie James Button, Corning Inc., May 7, 1997 and earlier documents.
[7] 3396052966 FCOTAC, Alcatel FO The production of telecommunication optical fibers by fibering requires increasingly weak dispersions around the specified nominal diameter and an absence of critical defects affecting the mechanical and optical characteristics of the fibers, but especially those affecting their lifetime. This is the case for "air-line" glass defects, or "bubble" or "delamination" coating defects, as well as the eccentricity of the glass in its polymer coating. Finally, increasing fibering speeds and high-frequency fluctuations of the diameter of the fibers require instruments which are faster that those currently used for visualizing and reducing these phenomena.

References [1] and [2] summarize the fundamental principles of light propagation in a transparent fiber, as described in FIG. 1, specifically when it is illuminated by a monochromatically-collimated light field which is consistent and perpendicular to the axis of the fiber. The deflection of the light by the fiber produces a system of interferometry fringes whose periods and phases depend on the index profiles: diameters, substances, homogeneity, concentricity. By analyzing these fringes according to the measurement angles, one may deduce precise information as to the conformity of the fiber to a model defined as an absolute reference. The quality of the measured signal, represented by the contrast and regularity of the fringes and by the signal's energy, depends on the fiber's optical quality, namely the absence of defects, homogeneity, and geometric regularity. Continuous high-speed analysis of the fringe contrast allows very small defects to be detected, such as bubbles in polymer coatings.

Reference [1] describes in detail the propagation relations and deduces from them a method for rapid measurement of diameter variations and a diameter measurement method by calibration on a standard fiber. The cited documents describe assemblies for measuring diameter variations by counting the fringe shift or the diameter by measuring the reference fringe period to a standard fiber period. Document [6] uses a Fourier transform processing method for diameter measurement and to detect small defects in the glass.

A method and an assembly that allows both dimensional measuring and control of glass fibers prior to coating (bare fibers), as well as dimensional measuring and control of the coatings, would be desirable. More generally, a method and an assembly that applies to any circular section, optically-transparent stem corresponding to FIG. 1 and presenting an R1, N1 and R2, N2 index profile would be desirable. No apparatus known to date allows absolute measurement of the diameter without contact, at more than 50 KHz, and statically with resolutions of a few hundredths of a micron including defect detection.

BRIEF SUMMARY OF THE INVENTION

Disclosed is a device for absolute, high-speed measurement of a diameter of an optical fiber and for detecting defects in the fiber, comprising two complementary signal processing systems including first and second sensors and first and second processing boards wherein angular calibration of the sensors is performed by directly deducing the absolute diameter of the fiber from the equations (4) and (7):

$$f(n,\theta)=\sin(\theta/2)+[n^2+1-2*n*\cos(\theta/2)]^{1/2} \quad (4)$$

$$M=[A/(B+\theta)]*[1+\sin^2\{N(D,\theta)*\pi+\phi\}]. \quad (7)$$

in which n represents N1 index of a substance, $\theta$ is a measurement angle, D is outer diameter, A is a signal amplitude in volts, B is a measurement angle, and M is a signal amplitude.

BRIEF DESCRIPTION OF THE FIGURES

The following descriptions should not be considered limiting in any way. With reference to the accompanying drawings, like elements are numbered alike:

FIG. 3 is a normal signal of a 125 um glass fiber;

FIG. 4 is a disturbed signal of a 125 um (lass fiber with a 4.8 um air-line;

DETAILED DESCRIPTION OF THE INVENTION

Figure 1:
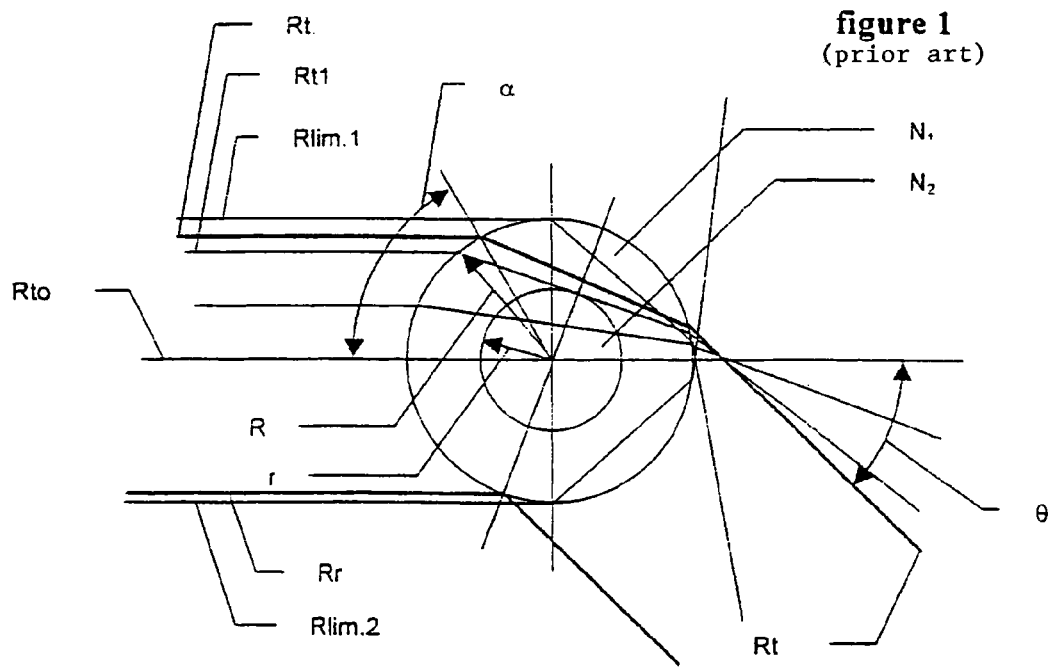
FIG. 1 is a cross-sectional view of an optically transparent stem.

FIG. 1 recalls propagation phenomena in a transparent cylindrical structure consisting of a ray center "1" and an index $N_1$, and a ray envelope "R" and an index $N_2$ for which the maximum r/R ratio is 0.5, as is habitual for telecommunication fibers. This structure represents, specifically, either a multi-mode glass fiber with its core (62.5/12.5 µm) or a monomode fiber or a coated glass fiber (125/245 µm). The indices of the two coating layers are considered close to glass in order to use the same model. However, one may apply the invention using models which take into account the index differences of the coating layers.

The propagation of light rays through the fiber has been widely studied and we will cite only the results of these studies. The reflected (Rr) and transmitted (Rt) bundles interfere infinitely all the way around the fiber. The model describing the bundles' contribution to the fringe system is expressed by:

$$s = \Sigma_i \psi(n, \theta, D, \lambda), \text{ in which:} \quad (1)$$

ψi Propagation relation of each laser line contributing to constitution of the signal at the same point.

n N1 index of the substance

θ Measurement angle

D Outer diameter

λ Laser wavelength

In an angle zone θ between 40° and 80°, two functions ψ corresponding to rays Rt and Rr largely dominate the others. We group the contributions of the other residual bundles (multiple reflections in the fiber) under the character ε, which reduces relation (1) to:

$$S = \Psi R_t + \Psi R_r + \epsilon; \quad (2)$$

The difference Δ between the two bundles ψ is expressed in terms of the outer diameter of the fiber "D", the index of the outer coating "n=$N_1$", the wavelength "λ," and the measurement angle "θ", according to references [1] and [2].

$$\Delta = D^* f(n, \theta) + \lambda/4 \text{ in which} \quad (3)$$

$$f(n, \theta) = \sin(\theta/2) + [n^2 + 1 - 2^* n^* \cos(\theta/2)]^{1/2} \quad (4)$$

Or in number of fringes:

$$N = \Delta/[\lambda] = (D/\lambda)^* f(n, \theta) + \frac{1}{4} \quad (5)$$

$$N(0) = (D/\lambda)^* (n^2 - 2^* n + 1) + \frac{1}{4} \quad (6)$$

Figure 2:
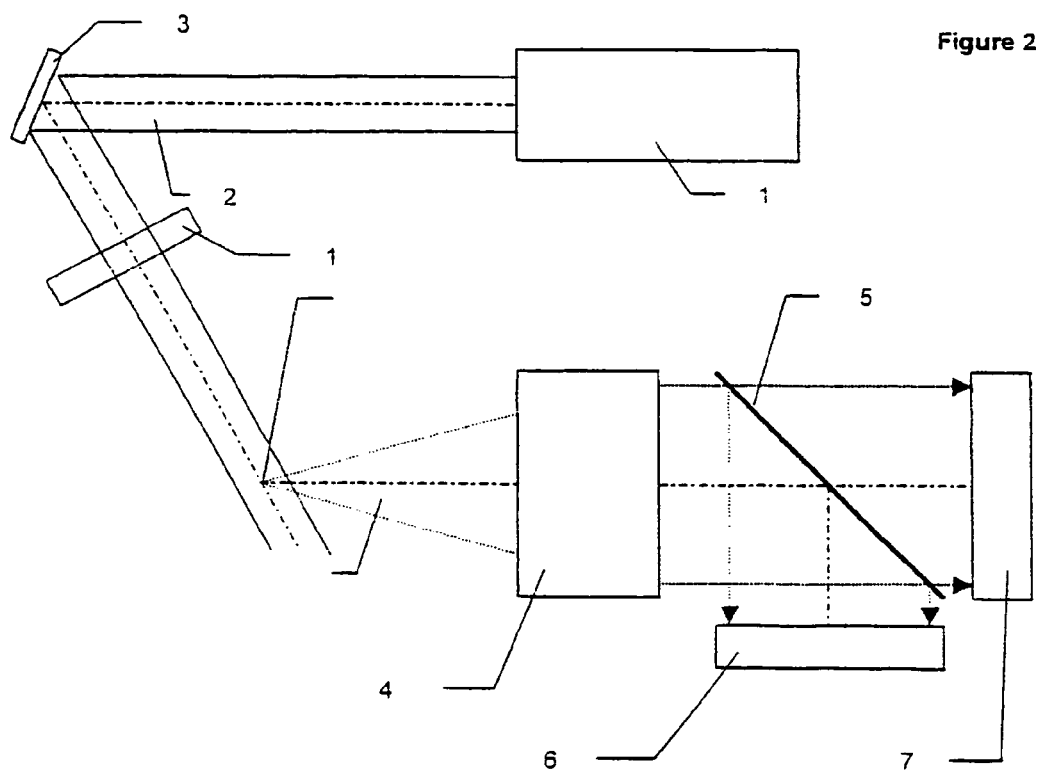
FIG. 2 is a schematic planar view of a device for absolute, high-speed measurement of a diameter of an optical fiber.

If each parameter λ, θ, and n is precisely known, the relations (3) and (4) constitute a reference model for the absolute measurement of D, without calibration constraint by a standard fiber. The parameter λ is precisely measurable or known from the laser (He). "N1" is the precisely known index of the outer layer of the fiber. θ must be measured on the instrument. Each elementary point of the sensor 6 FIG. 2 which is used must therefore correspond to a precise angle value.

The method includes digital processing of the signal which identifies a parametrable model on the signal and which leads directly to absolute measurement of the diameter. The method also may include a high-speed, analog method for measuring diameter variations with very high resolution; lastly, it resides in the correlation of the results of these digital and analog methods to provide a high-speed, absolute measurement method. An element of the method is found in the optical quality of the signal, characterized by the fringe contrast. The permanent analog control of the contrast, included in the apparatus, also aids in the detection of possible defects in the fiber.

Absolute Measurement of the Diameter

This measurement is performed by digital processing of a signal coming out of a sensor 6 (FIG. 2), consisting, in our case, of a CCD barrette placed between 40 and 80° in relation to the origin of the laser bundle. In the experimental assembly, the angle window is 24°. The digital processing is characterized by a weak measuring frequency, currently 10 Hz.

A model for representing the fringe system produced by Rt and Rr may be written as:

$$M = [[A/(B+\theta)]^* [1 + \sin^2\{N(D,\theta)^* \pi + \phi\}], \text{ and} \quad (7)$$

$$S = M + [\epsilon] \quad (8)$$

Figure 10:
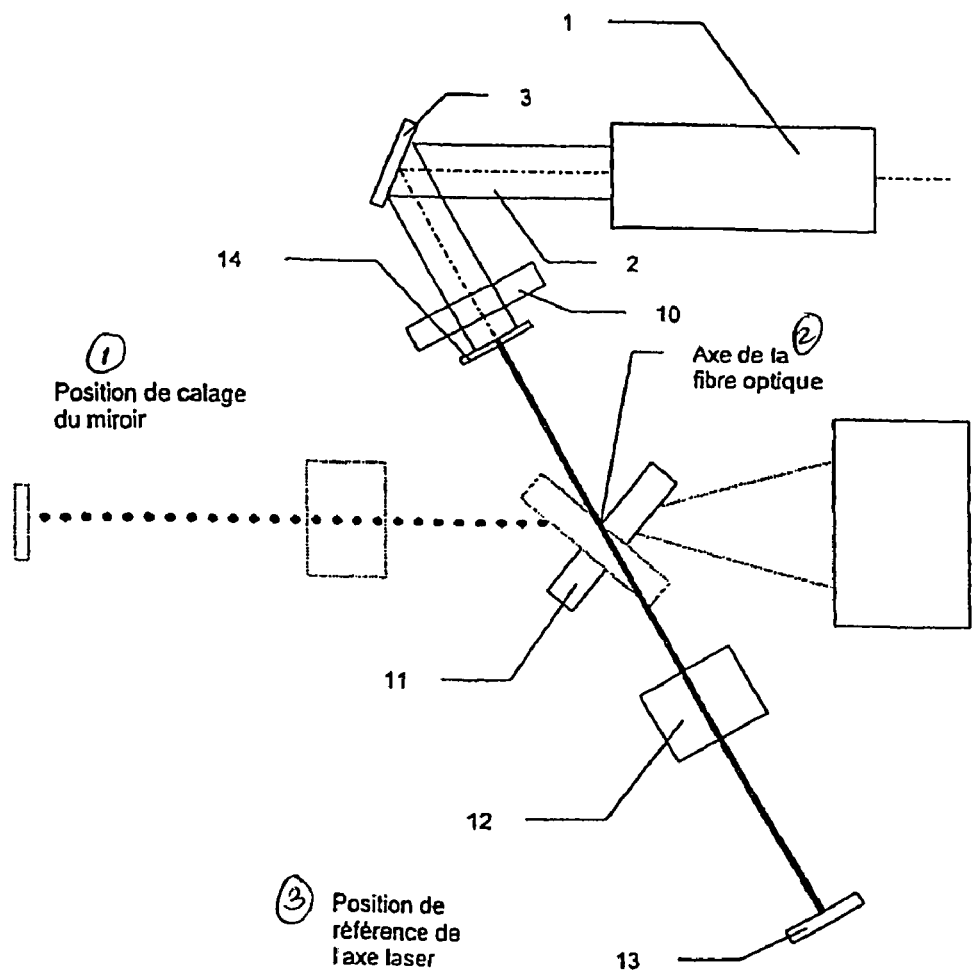
FIG. 10 is an expanded schematic planar view of the device for absolute, high-speed measurement of a diameter of an optical fiber as shown in FIG. 1.

The identification of the model M which is closest to the fringe system S leads to determining A, B, D, and φ minimizing the residual s. All identification methods can be used. We use a least square minimization method, first on the period by optimization of D and φ, then on amplitude. The parameters A and B make it possible to identify an approach amplitude profile allowing defects to be detected. Their values are approximately proportional to the diameter (energy of signal), which makes it possible to initialize them after the apparatus is adjusted. Only the value of D, in N(D,θ) is of interest to us for the measurement. φ is a parameter that allows maximal adjustment of the phase of the model to that of the signal;

The angular calibration of the sensor is performed with reference to the direction of the measuring laser's axis of incidence taken as angle value 0. To identify the angle positions of the pixels, the assembly in FIG. 10 is used. The optical bench of the measuring apparatus is mounted on a test bench consisting of an optical slit (14) for limiting the laser's field and energy on the sensors, a high-precision angle coder centered on the axis of the fiber (axis of the apparatus), an integral unit made up of optics focusing (12) the laser bundle and a sensor (13) providing proportional voltage to the position of the laser spot. The unit (12)(13) is turned angularly until the sensor (13) indicates the position of the laser bundle at 0 volts. The angle coder is then integrated into the unit (12)(13) and initialized at zero on the axis of the laser. The unit (12)(13) is then turned at any angle, at 110°, for example, in order to allow a mirror to be placed and angularly referenced on the fiber axis. The mirror and the unit (12)(13) are adjusted until 0 volts is indicated on the sensor (13). Next, the mirror is integrated into the coder, the angle value $\theta_0$, corresponding to 0 volts on the coder, is recorded, and the unit (12)(13) is taken apart. The mirror is then angularly referenced. The axis of the laser deflected by the mirror will then be $A=2^*(\pi-\theta)-\theta_0$. By turning the mirror (11), the laser spot is displaced onto the sensors 6 and 7. One may therefore record point by point the angle positions of the pixels and identify the angle transfer function=f(Pixels) including the optical system 4.

The fringe system in an angle zone of 24° taken between 40 and 80°, for a fiber D=125 μm, λ=780 nm, and n=1.478, is shown in FIG. 3. The precise measurement of the signal's period evolution measured as a function of the angle allows the identification of D in the model.

A first approach consists of identifying the parameters D and φ by minimizing the differences between the model and the measured signal, between θ1 and θ2, which correspond to the angle span of the CCD barrette. In this approach, we do not take into account the phase of the fringe system but only the period in terms of the angle.

We obtain measurement stability and reproducibility greater than 0.02 μm. The total uncertainty calculated on D is lower than ±0.15 μm. These uncertainties are as follows: Index: for silica known with negligible uncertainty in terms of the wavelength. For the coatings, the parameters which allow the indices to be calculated are provided with precision by the manufacturers.

Laser wavelength: For a gas laser, the values are also known with great precision and negligible uncertainty. For a stabilized diode laser, the wavelength is measured at ±0.2 nm out of 780, or ±0.025%.

Angle values: The resolution of the sensor is 3 arcseconds with a cumulative total uncertainty of the calibration of 1 arcminute, or 0.024 on 70° (4200 arcminutes). The total uncertainty of the apparatus would then be 0.05% of the diameter, or ±0.06 μm on 125 μm. To these uncertainties must be added imperfections in the fiber (ovality, local optical disturbances, residual "ε" signals) which reduce the total uncertainty to an estimated value of ±0.15 μm.

The angle span for measurement located between 58 and 82° corresponds to approximately 30 fringes. Relation (6) shows that at θ=0, N(0) varies proportionally to the diameter; that is, that the phase of Rt from S to θ=0 varies proportionately to the diameter. If the model is sufficiently certain to determine the phase of the wave (Rt, FIG. 1) crossing the fiber for θ=0, then it is possible to measure the fiber's diameter with very high precision. In this case, the phase "φ" identified in the first approach takes on its full meaning. It is then possible, starting from the angle span of measurement of the CCD, to dispel any doubt as to the number of fringes of the model, between θ=0 and a fringe on the CCD. Indeed, the total uncertainty of the measurements taken in an angle window of 24° is 0.15%. The number of fringes between 0 and 70° is approximately 180 at λ=780 nm. The uncertainty as to the number of fringes between 0 and 70° is then 0.15%*180=0.28, or quite a bit less than a half-fringe. One then adds to the model the phase of S at the origin of the angles to obtain greatly improved measurement precision. Function (4) is taken into account in the angle span from 0 to $O_o$ on the CCD.

The advantage of this measurement method by model adaptation is that it is free of the fluctuations linked to variations in the signal's residual modulations in the angle span for measurement. Indeed, it takes into account the model of N in the totality of the measurement angle between 0° and θ. This gives great stability to the digital measurement, on the same order as the analog measurement which we will discuss below.

However, uncertainties remain regarding the geometric dispersion of the fiber in relation to the model that led to the establishment of basic relations: circularity of the fiber, defects in cylindricity, as well as defects linked to divergence of the laser bundle. Although these defects are very limited when reduced to the diameter, they do not, however, make it possible to create an absolute measurement apparatus with the precisions corresponding to the achieved resolutions. Moreover, the best measurement methods that could allow us to validate the metrological results do not, to date, perform better than ±0.15 μm. This means that the first evaluation, by angle difference, is sufficient in this configuration.

Rapid Measurements of Diameter Variations

In relation to a given angle position, the fringe shift represents the result of the variation of all of the fringe periods between the angle origin and the angle position of the measurement, plus the phase variation at the angle origin. This phase measurement method at point θ has the advantage of being very stable, very reproducible, very sensitive to diameter variations, and insensitive to the residual modulations of the fringe system. It differs from the digital measurement method but leads to the same resolutions. This method gives only diameter variations but does so at high speed, as opposed to the absolute, digital method, which is slow. These methods are therefore complementary for ensuring both absolute measurement and high speed.

The diameter variation leading to this shift is expressed as:

$$dD=-\lambda d*N/f(n,\theta) \quad [1] \qquad (9)$$

Figure 9:
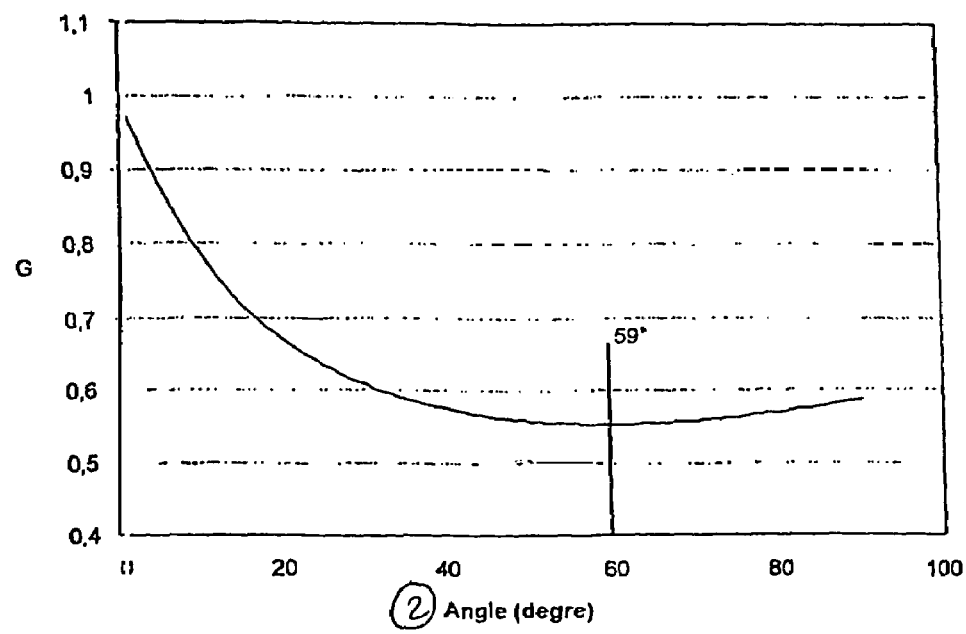
FIG. 9 is a graph illustrating signal period evolution.

The fringe pitch as a function of angle θ is shown in FIG. 9. One sees that the fringe pitch remains essentially constant in the zone 60°±10°. This characteristic allows sensors spaced by a constant corresponding to fringe pitch to be placed in this zone. It is also interesting in terms of measuring the period (frequency) by Fourier transform [6]. From relation (9), one may extract a rapid measurement of diameter variations at high speed and with high resolution. For example, for a 70° angle, a 780 nm wavelength, and a 1,476 glass index, the shift dN=¼ fringe represents a diameter variation of 0.13 μm. In our method, one easily obtains a resolution of 1⁄32 fringe, or 0.01 μm.

Assemblies for measuring diameter variations can be found in the literature. They are based on methods for counting binarized S1, S2 signals whose minimum resolution remains ¼ fringe. The difference in our method consists of binarizing the fringe signal differently, which also allows the shift to be counted in ¼ fringe increments as well as to interpolate this shift within an increment.

Figure 7:
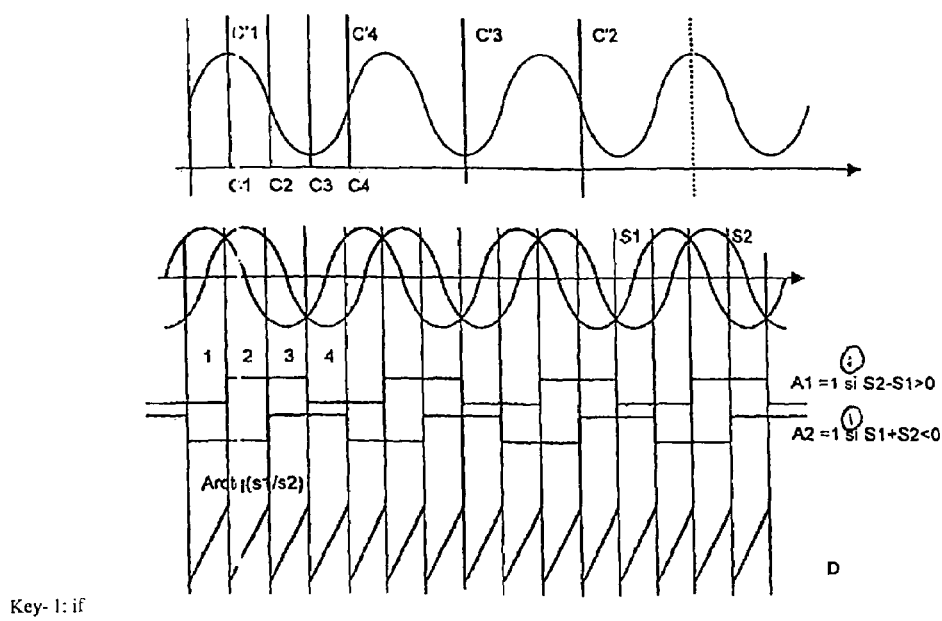
FIG. 7 is a graph illustrating signal pitch.
Figure 8:
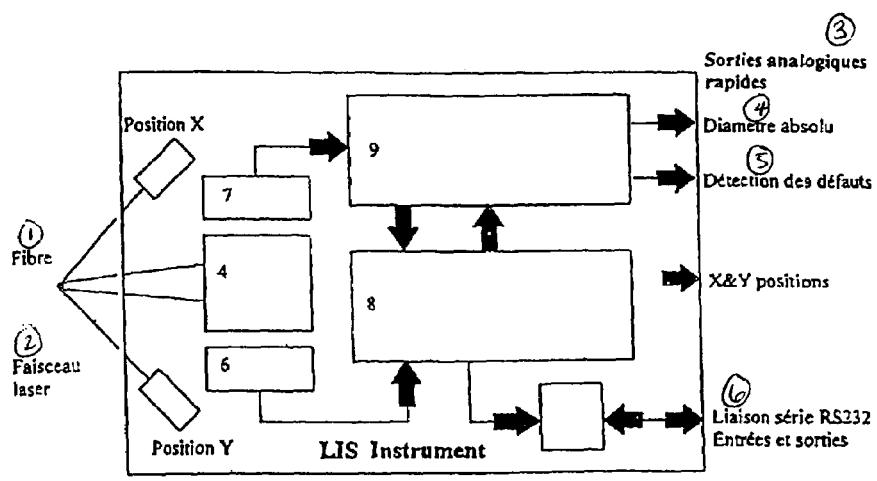
FIG. 8 is a schematic view of an LIS instrument.

This measurement is made by placing sensors at a pitch corresponding to a proportion of the nominal fringe pitch; see FIG. 7. The multiple advantages of this approach are: The measurement does not take into account signal amplitude residual modulations or period fluctuations, but only the fringe phase in relation to the sensors. This makes the measurement insensitive to fringe amplitude modulations.

The fringe phase shift results from the variation of all of the fringes starting at the angle origin (axis of the laser), which provides very high sensitivity. One obtains a resolution and reproducibility of 0.01 μm.

This measurement allows the implementation of continuous analog methods with high bandwidths, 75 KHz in our case.

Figure 6:
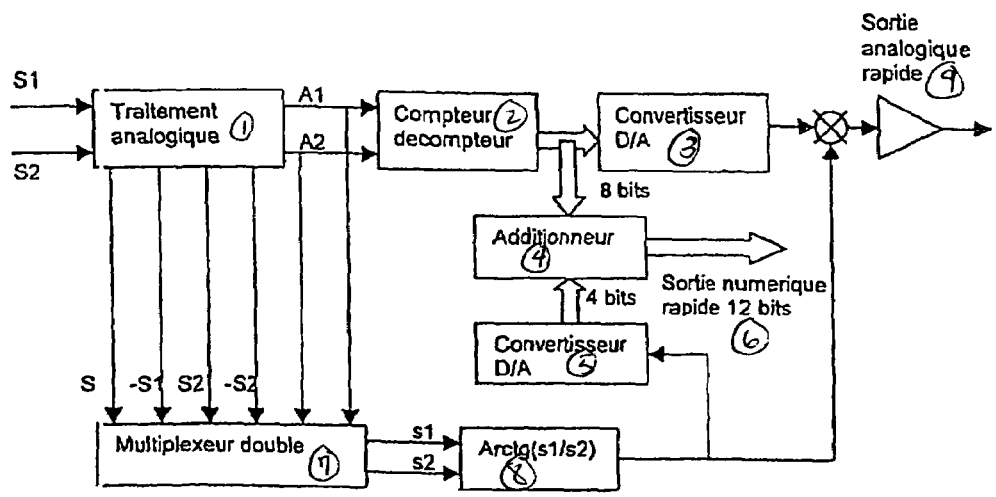
FIG. 6 is a block diagram illustrating a method of implementing the device for absolute, high-speed measurement of a diameter of an optical fiber.

FIGS. 6 and 7 present the principle of this high-resolution measurement. As is known, a series of optical sensors (pixels) is placed so as to be spaced in an odd number of ¼ fringes from the optical signal. One may, for example, use the sensors C1 to C4 (FIG. 7) spaced at ¼ fringe or C'1 to C'4 spaced at ¾ fringe. The latter arrangement allows the use of sensors whose pitch between pixels is greater than the fringe pitch to be measured. Over several periods, the association of sensors C1 to C4 is reproduced, and they are connected in parallel so as to add up the C1 signals which share the same index. The sensitive surfaces of the sensors must not exceed ¼ of the fringe pitch in order to obtain a contrast hop in the signals. In our case, we chose ⅕ and obtained a satisfactory result. The following analogic sum of the signals is then found:

$$S1=C1-C3$$

$$S2=C2-C4$$

in order to eliminate direct components.

Instead of binarizing S1>0 and S2>0, as is commonly done to obtain 2 counting signals, the following conditions are binarized:

$$A1=f[S1-S2>0]$$

$$A2=f[S1+S2<0]$$

The two binary signals A1 and A2 serve two purposes: One is to count the shift of S1 and S2 by ¼ period, as is known in the art; the other is to switch the signals S1, –S1, S2, and –S2 on a calculation circuit of the arctangent (s1/s2) as a function of the four combinations between A1 and A2 represented as 1 to 4 in FIG. 7. (/Ai logic complement of Ai).

/A1*/A2:s1/s2=S2/S1

A1*/A2:s1/s2=–S1/S2

A1*A2:s1/s2=–S2/–S1

/A1*A2:s1/s2=S1/–S2

FIG. 6 shows a block diagram of the realization of an analog measurement following this principle starting from signals S1 and S2. The signals A1 and A2 control a double multiplexer which alternatively switches the four inputs S1, –S1, S2, –S2 towards s1 and s2 according to the above information. Analog measurement trials yielded an ENR1 entry in terms of reproducibility.

At initialization, the digital and analog measurement methods are united in order to filter the dispersions between the two methods efficiently. This is advantageous in production, when signal fluctuations between two measurements may be considered hazardous. To do this, we compare the digitally and analogically measured values sampled at the same moments by averaging the "n" last measurements. The residual dispersions of the digital measurement in the first processing phase (diameter calculated between two angle values) are then weighted and the absolute analog value is initialized according to the difference in the averages and not on the difference in the instant measurements.

Defect Detection

Defects are essentially "air-lines" (small tubes of air) in the glass fibers, namely localized surface defects.

Defects in the coatings include air bubbles, inclusion of unmelted materials, delaminations (layer of gas between the glass and the coating), overthicknesses, underthicknesses, and eccentricity.

In this assembly, we are considering only real-time detection of optical disturbances produced by air-lines, bubbles, delaminations, and inclusions. The diameter variations are taken into account by simple comparison of the rapid analog output with programmed or adjusted thresholds.

Two parameters are used to characterize the quality of the optical signal: energy, which increases with the size of an air-line, and especially fringe contrast (difference between the maxima and minima of S1 and S2), which is a fundamental element for this measurement method. The absence of contrast on the fringes prevents proper measurement.

Real-time energy is obtained by the sum of currents coming from the analog sensor's photodiodes. Real-time contrast is obtained by taking the maximum of the four signals S1, –S1, S2, –S2. This signal is naturally fluctuating since the S1s are sinusoids.

The appearance of a defect, even a small one, produces either a marked drop in contrast or a saturation. Regardless of the type of defect, the contrast always reacts much more sensitively than the energy does. This is the parameter we are considering for defect detection.

Figure 5:
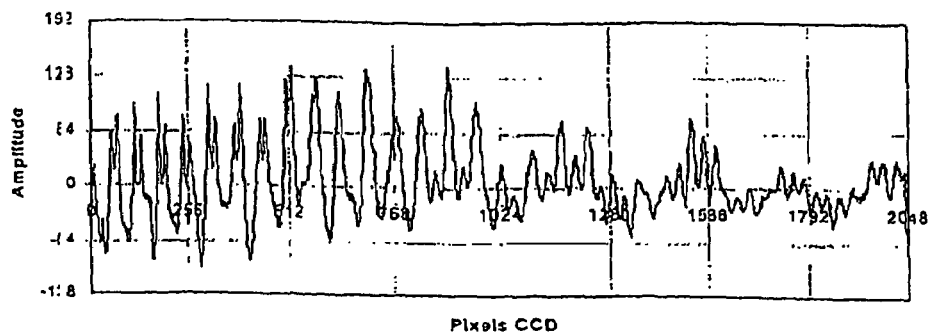
FIG. 5 illustrates a signal comparison between the signals of FIG. 3 and FIG. 4.

For more subtle air-line defects, digital processing extracts the component of the measured signal that does not correspond to an acceptable distribution of the fringe amplitude and period (see FIG. 3 (normal signal), FIG. 4 (disturbed signal), FIG. 5 (difference of the signals in FIGS. 3 and 4)).

The invention claimed is:

1. A method for measuring the diameter of an optical fiber and for detecting defects in the fiber, the method comprising:
   directing a beam of a laser at the fiber, radially, to produce an interference pattern;
   providing a first sensor receiving said interference pattern in an angle span, with respect to an axis of said laser, through an optical system;
   providing a first processing board connected to said first sensor for analyzing said interference pattern received by said first sensor;
   calibrating said first sensor so that each of several points of said first sensor corresponds to a determined value for said angle with respect to said axis of said laser axis;
   using said processing board for calculating the values for A, B, D and φ so that a theoretical curve of the interference pattern, represented by:

$$M = \frac{A}{B+\theta} \times [1 + \sin^2\{N(D, \theta) \times \pi + \varphi\}]$$

$$N(D, \theta) = \frac{D}{\lambda} \times \left[\sin\frac{\theta}{2} + \left(n^2 + 1 - 2n \times \cos\frac{\theta}{2}\right)^{1/2}\right] + \frac{1}{4}$$

wherein:
M is a signal amplitude, A is a calibration parameter for the signal amplitude, B is a calibration parameter for the angle, φ is a calibration parameter for the phase, N is a number of fringes, θ is a measurement angle with respect to said axis of said laser, D is a fiber diameter, and λ is a laser wavelength,
   corresponds to said interference pattern received by said first sensor, in order to obtain an absolute measurement of said fiber diameter D.

2. A method according to claim 1, further comprising:
   providing a second sensor receiving said interference pattern in said angle span, with respect to said axis of said laser, through said optical system, said second sensor being preliminarily calibrated so that each of several points of said second sensor corresponds to a determined value for said angle with respect to said axis of said laser, said second sensor being optically aligned with said first sensor;
   providing a second processing board connected to said second sensor for analyzing said interference pattern received by said second sensor, said second processing board being able to determine variations in the fiber diameter by analyzing shift in said fringes via to a relation:

$$dD = -\lambda \times \frac{dN}{\sin\frac{\theta}{2} + \left(n^2 + 1 - 2n \times \cos\frac{\theta}{2}\right)^{1/2}}.$$

3. A method according to claim 2, wherein said calibrating of said first sensor and said second sensor includes:
   providing a calibration bench external to said first sensor and said second sensor and an angle coder whose center is located on an axis of the fiber when the fiber present;
   referencing said angle coder with respect to said laser axis using an optic focusing and a voltage sensor that provides proportional voltage to a position of a laser spot;

referencing a mirror located on said axis of the fiber, when present, using said angle coder, said optic focusing and said voltage sensor;

fixing said mirror and said angle coder;

deflecting said laser angularly with said mirror onto successive points of said several points of said first sensor and said second sensor through said optical system, said deflecting precisely locating the angle positions of said successive points via to said angle coder.

4. a method according to claim 3, wherein said first processing board periodically provides an absolute value of said fiber diameter via a digital analysis and, at the same time, said second processing board continually provides a relative value of the variation of said fiber diameter via an analog analysis, wherein said absolute value of said fiber diameter provided by said first processing board is used to initialize said second processing board to provide a continuous, rapid, and absolute measurement of said diameter.

5. A method according to claim 4, further comprising:

generating, from said several points of said second sensor, two sinusoidal signals and two logic signals allowing said digital analysis of said fringe shift per quarter period;

interpolating between each switching of at least one of said two logic signals and a continuous variation of said fringe phase by calculating an appropriate arctangent between said two sinusoidal signals;

adding of results of said analysis and said interpolation to provide said continuous, rapid, and high-resolution measurement in said broad variation span of the diameter.

6. A method according to claim 5, further comprising:

detecting fringe contrast loss in order to detect, in real time, by analog analysis, presence of defects in the fiber; and using said amplitude difference between a theoretical model and a measured signal to detect very small defects by digital processing.

7. A device for measuring diameter of an optical fiber and for detecting defects in the fiber, comprising:

a laser adapted to radially direct a beam at the fiber to produce an interference pattern;

an optical system configured to receive the interference pattern in an angle span, with respect to an axis of the laser, and configured to project said pattern to a first sensor and a second sensor, optically aligned and located in a focal plane of said optical system;

a first processing board connected to said first sensor, said first board being configured for analyzing said interference pattern received by said first sensor and, consequently, configured to periodically determine absolute diameter of the fiber; and a second processing board connected to the second sensor, said second board being configured for analyzing the interference pattern received by the second sensor and, consequently, configured to continually determine fiber diameter variations by analyzing fringes shift, wherein said first board and said second processing board are connected so that said second processing board is initialized by said first processing board, in order to provide a continuous, rapid and absolute measurement of the diameter of the fiber.

8. A device according to claim 7, wherein said angle span of said sensors is between 40° and 80°.

* * * * *